(12) United States Patent
Lund

(10) Patent No.: US 11,855,390 B2
(45) Date of Patent: Dec. 26, 2023

(54) RACK MOUNT

(71) Applicant: DRÄGERWERK AG & CO. KGAA, Lubeck (DE)

(72) Inventor: Peter Andrew Lund, Nashua, NH (US)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 0 days.

(21) Appl. No.: 17/875,079

(22) Filed: Jul. 27, 2022

(65) Prior Publication Data

US 2022/0368075 A1 Nov. 17, 2022

Related U.S. Application Data

(63) Continuation of application No. 16/958,972, filed as application No. PCT/IB2017/001733 on Dec. 27, 2017, now Pat. No. 11,431,127.

(51) Int. Cl.
| | |
|---|---|
| *H01R 13/15* | (2006.01) |
| *H01R 13/645* | (2006.01) |
| *A61B 5/00* | (2006.01) |
| *H01R 29/00* | (2006.01) |
| *H01R 33/92* | (2006.01) |

(52) U.S. Cl.
CPC ......... *H01R 13/6456* (2013.01); *A61B 5/742* (2013.01); *H01R 29/00* (2013.01); *H01R 33/92* (2013.01); *A61B 2560/06* (2013.01); *A61B 2562/227* (2013.01); *H01R 2201/12* (2013.01)

(58) Field of Classification Search
CPC .... H01R 13/6456; H01R 29/00; H01R 3/622; H01R 13/623; A61B 5/742; A61B 2560/06; A61B 2562/227
See application file for complete search history.

(56) References Cited

U.S. PATENT DOCUMENTS

| | | | | |
|---|---|---|---|---|
| 3,551,879 | A | * 12/1970 | Waller, Sr. ........... | H01R 13/639 439/369 |
| 5,208,436 | A | * 5/1993 | Blankenship ............ | H05H 1/36 219/121.54 |
| 7,175,478 | B2 | * 2/2007 | Ollivier .............. | H01R 13/5224 439/669 |
| 2002/0117849 | A1 | * 8/2002 | Bailey ................. | F16L 27/0804 285/123.15 |
| 2008/0090434 | A1 | * 4/2008 | Lin ........................ | H01R 13/60 439/131 |

(Continued)

*Primary Examiner* — Phuong Chi Thi Nguyen
(74) *Attorney, Agent, or Firm* — Nolte Lackenbach Siegel

(57) ABSTRACT

A system of mated connectors includes a connector having one or more connector quadrants comprising electrical contacts and a mating connector detachably secured to the connector. The mating connector includes one or more mating quadrants and electrical contacts. The mating connector configured to provide electrical coupling to the connector detachably secured thereto. The electrical contacts of a first quadrant of connector quadrants have a first predetermined pin-out and the electrical contacts of a second quadrant of the connector quadrants have a second predetermined pin-out. The electrical contacts of each quadrant of a first pair of the mating quadrants have the first predetermined pin-out and the electrical contacts of each quadrant of a second pair of the mating quadrants have the second predetermined pin-out.

20 Claims, 6 Drawing Sheets

(56) References Cited

U.S. PATENT DOCUMENTS

2010/0104355 A1* 4/2010 Sugimoto ............ G02B 6/3897
 403/292
2015/0079829 A1* 3/2015 Brodsgaard ............ H01R 24/84
 439/284

* cited by examiner

RACK MOUNT

CROSS REFERENCE TO RELATED APPLICATION

This application is a continuation of co-pending U.S. patent application Ser. No. 16/958,972, filed Jun. 29, 2020, which was a 371 nationalization of PCT/IB2017/001733, filed Dec. 27, 2017, the entire contents of which applications are hereby incorporated by reference as though fully set forth herein.

TECHNICAL FIELD

The subject matter described herein relates to a rack mount for use in connection with a patient monitor device and/or a physiological patient parameter measurement device.

BACKGROUND

During the course of providing healthcare to patients, practitioners typically monitor patient medical parameters of a patient using one or more monitoring devices such as a patient monitor device and/or a physiological patient parameter measurement device. These are usable by healthcare practitioners (e.g., nurses, doctors, physician assistants, or any other person charged with providing a healthcare service to a patient) in monitoring a patient and determining a course of healthcare to be provided to the patient. Such devices can be transportable devices that can be moved throughout a patient monitoring environment and mounted to a rack mount for stationary use. Coupling a patient monitor device and/or a physiological patient parameter measurement device to a rack mount can be dictated by stationary orientations of the rack mount.

SUMMARY

In one aspect, a system of mated connectors includes a connector comprising one or more connector quadrants comprising electrical contacts and a mating connector detachably secured to the connector. The mating connector includes one or more mating quadrants and electrical contacts. The mating connector is configured to provide electrical coupling to the connector detachably secured thereto. The electrical contacts of a first quadrant of connector quadrants have a first predetermined pin-out and the electrical contacts of a second quadrant of the connector quadrants have a second predetermined pin-out. The electrical contacts of each quadrant of a first pair of the mating quadrants have the first predetermined pin-out and the electrical contacts of each quadrant of a second pair of the mating quadrants have the second predetermined pin-out.

In another aspect, a connector includes one or more connector quadrants configured to provide electrical coupling to a mating connector comprising one or more mating quadrants. The connector and the mating connector each include electrical contacts. The electrical contacts of a first quadrant of connector quadrants have a first predetermined pin-out and the electrical contacts of a second quadrant of the connector quadrants have a second predetermined pin-out. The electrical contacts of each quadrant of a first pair of the mating quadrants have the first predetermined pin-out and the electrical contacts of each quadrant of a second pair of the mating quadrants have the second predetermined pin-out.

In another aspect, a mating connector includes one or more mating quadrants configured to provide electrical coupling to a connector comprising one or more connector quadrants. The connector and the mating connector each include electrical contacts. The electrical contacts of a first quadrant of connector quadrants have a first predetermined pin-out and the electrical contacts of a second quadrant of the connector quadrants have a second predetermined pin-out. The electrical contacts of each quadrant of a first pair of the mating quadrants have the first predetermined pin-out and the electrical contacts of each quadrant of a second pair of the mating quadrants have the second predetermined pin-out.

In some variations, the first quadrant of the connector quadrants and the second quadrant of the connector quadrants are nonadjacent.

In other variations, the remaining two connector quadrants have no electrical contacts.

In yet another aspect, a connector includes one or more connector quadrants configured to provide electrical coupling to a mating connector comprising one or more mating quadrants. One of the one or more connector quadrants includes electrical contacts having a predetermined pin-out. In some variations, the electrical contacts of at least one quadrant of the one or more mating quadrants has the predetermined pin-out. In other variations, the remaining three connector quadrants have no electrical contacts.

In another aspect, a mating connector includes one or more mating quadrants configured to provide electrical coupling to a connector comprising one or more connector quadrants. One of the one or more connector quadrants includes electrical contacts having a predetermined pin-out. In some variations, the electrical contacts of at least one quadrant of the one or more mating quadrants has the predetermined pin-out. In other variations, the remaining three connector quadrants have no electrical contacts.

In some variations, the connector and the mating connector can be a keyed connector and at least one of the one or more connector quadrants and at least one of the one or more mating quadrants are keyed quadrants.

In other variations, the connector can be a male connector having one or more electrical connection pins and the mating connector can be a female connector having one or more electrical sockets configured to accept the one or more electrical pins of the connector.

In some variations, the mating connector can be a male connector having one or more electrical connection pins and the connector can be a female connector having one or more electrical sockets configured to accept the one or more electrical pins of the mating connector.

In yet another variation, a rack mount provides for electrical connections between a patient monitor and one or more physiological sensors affixed to a patient. The rack mount includes a monitor mount, a physiological patient parameter measurement device, and a mount connector affixed to the monitor mount. The mount is configured to receive and detachably secure to the patient monitor. The physiological patient parameter measurement device mount is configured to (i) rotate and orient in a first orientation or a second orientation and to (ii) receive and detachably secure a physiological patient parameter measurement device. The mount connector includes one or more quadrants configured to provide electrical coupling between the patient monitor and the physiological patient parameter measurement device detachably secured to the mount connector. The first orientation can be a vertical orientation and the second orientation can be a horizontal orientation.

In some variations, the monitor mount can include an articulating leg enclosed within at least a portion of the monitor mount at a first end of the monitor mount. The articulating leg can be configured to retract and extend between at least two positions. The monitor mount can be affixed to a second end of the articulating leg. The articulating leg can be configured to extend or retract in a vertical direction relative to the monitor mount.

In some variations, the at least two positions can include an extended position with the articulating leg fully extended in a vertical direction and the mount connector is at a distance farthest from the monitor mount. The at least two positions can include a stowed position with the articulating leg fully retracted within the monitor mount and the mount connector is at a distance closest to the monitor mount. The articulating leg can be biased to the stowed position.

In other variations, mount connector is a keyed connector and at least one of the one or more quadrants can be a keyed quadrant.

In some variations, the physiological patient parameter measurement device can include a device connector configured to receive the one or more quadrants of the mount connector.

In other variations, the rack mount can include the patient monitor detachably secured to the monitor mount and the physiological patient parameter measurement device coupled between the one or more physiological sensors and the physiological patient parameter measurement device.

In some variations, the mount connector can be configured to facilitate power and/or data transmission between the patient monitor detachably secured to the monitor mount and the physiological patient parameter measurement device detachably secured to the physiological patient parameter measurement device mount. In some variations, the mount connector can be a male connector having one or more electrical connection pins and the device connector can be a female connector having one or more electrical receptacles configured to accept the one or more electrical pins of the mount connector. In other variations, the device connector can be a male connector having one or more electrical connection pins and the mount connector can be a female connector having one or more electrical receptacles configured to accept the one or more electrical pins of the device connector.

In other variations, the mount connector can include one quadrant, two, electrically redundant quadrants, or two, electrically different quadrants.

In other variations, the physiological patient parameter measurement device mount is a pod rack and the physiological patient parameter measurement device is a pod module.

The subject matter described herein provides many technical advantages. For example, the current subject matter provides for flexible utility and/or usability of one or more patient monitoring devices. Use of the subject matter herein can provide for a single rack mount for mounting of a patient monitor and physiological patient parameter measurement device. A mount connector of the rack mount can facilitate detachable coupling of the physiological patient parameter measurement device in a vertical or a horizontal direction. When coupled to the mount connector, the physiological patient parameter measurement device can be electrically coupled to a patient monitor that is also coupled to the rack mount for the transmission of data and/or power. Additionally, at least two quadrants of a mount connector as described herein can provide for redundant coupling configurations that facilitate coupling of a device connector to a mating mount connector in a vertical orientation of approximately 0 degrees and a horizontal orientation of approximately 90 degrees.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

Like reference symbols in the various drawings indicate like elements.

DETAILED DESCRIPTION

A single rack mount device can include a monitor mount and a mount connector for mounting of a patient monitor device and/or a physiological patient parameter measurement device. A mount connector can facilitate electrical coupling of a physiological patient parameter device when oriented in either a vertical or a horizontal direction to a monitor coupled to a monitor mount. When coupled to the mount connector, the physiological patient parameter measurement device can be electrically coupled to a patient monitor that is also coupled to the rack mount for the transmission of data and/or power.

Figure 1:
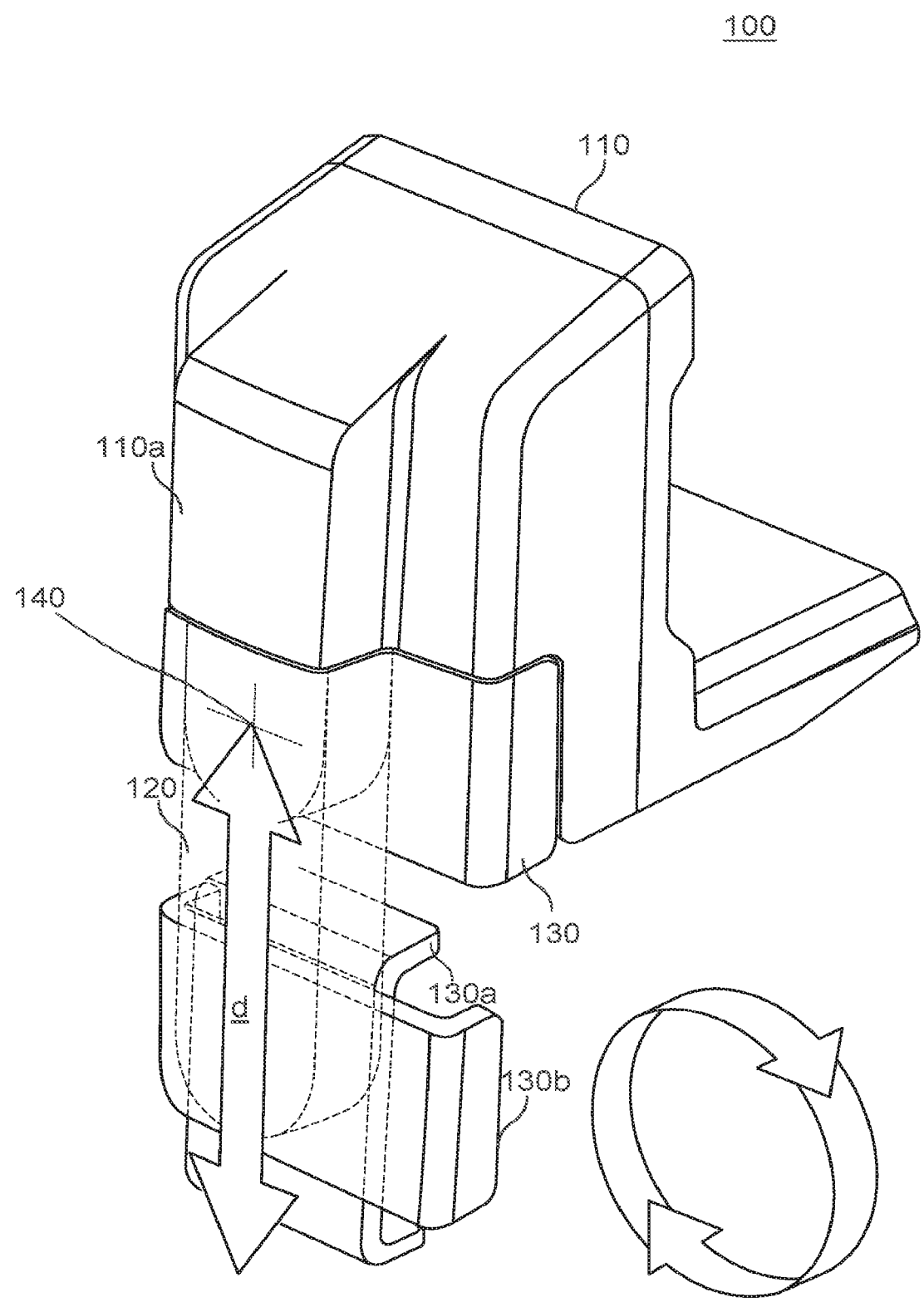
FIG. 1 illustrates a back perspective view of an example rack mount.

FIG. 1 illustrates a back perspective view of an example rack mount 100. Rack mount 100 can include a monitor mount 110. Monitor mount 110 can be configured to receive and detachably secure to a patient monitor (not shown). Rack mount 100 can also include an articulating leg 120 partially enclosed, at a first end, within a rear portion 110a of the monitor mount 110. A mount connector 230 of FIG. 2 can be affixed to articulating leg 120 in a stationary position at a second end of articulating leg 120 (e.g., the second end being opposite of the first end which is partially enclosed by monitor mount 110). Electrical cabling can run internal to articulating leg 120 to interconnect the mount connector 230 to one or more patient monitors detachably coupled to monitor mount 110. Articulating leg 120 can retract and extend between at least two positions, such as a stowed position and a fully extended position, which will be explained in detail to follow in FIGS. 4-6. Articulating leg 120 can retract and extend in a vertical direction relative to monitor mount 110. For illustration purposes, a distance, d, that articulating leg 120 can travel can be measured by the difference between a center point 140 of a mount connector 230 of FIG. 2 in the stowed position and a current position of the center point 140 when articulating leg 120 is any position other than stowed.

Rack mount 100 can also include a physiological patient parameter measurement device mount 130. Physiological patient parameter measurement device mount 130 can be configured to receive and detachably secure a physiological patient parameter measurement device 210 of FIG. 2. Physiological patient parameter measurement device mount 130 can be affixed to the second end of articulating leg 120. Physiological patient parameter measurement device mount 130 can be configured to rotate and orient in a first orientation such as a vertical orientation relative to articulating leg 120 as illustrated by vertically oriented physiological patient parameter measurement device mount 130a. Physiological patient parameter measurement device mount 130 can also be oriented in a second orientation such as a horizontal orientation relative to articulating leg 120 as illustrated by horizontally oriented physiological patient parameter measurement device mount 130b. Mount connector 230 of FIG. 2 remains stationary during rotation of physiological patient parameter measurement device mount 130.

Figure 2:
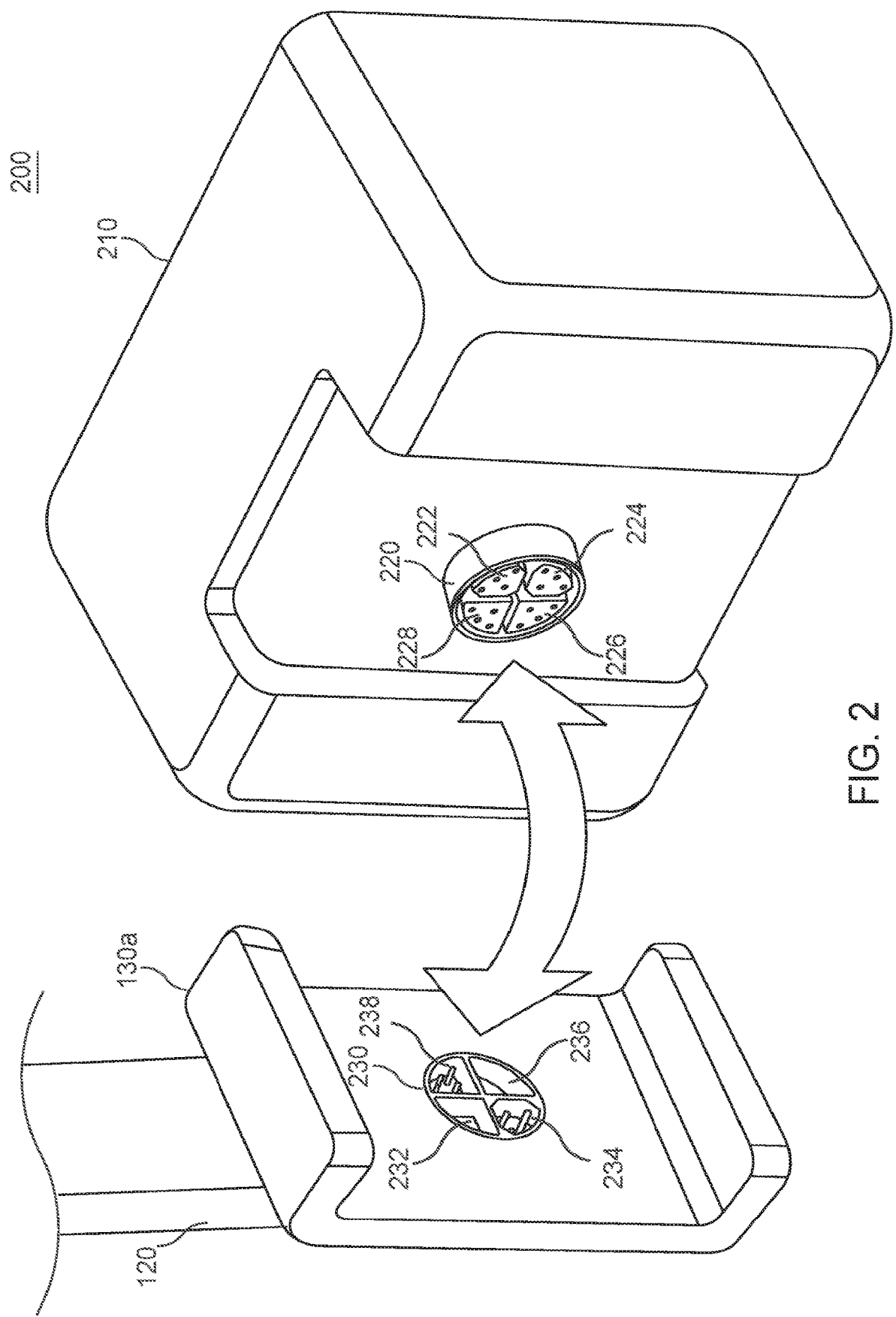
FIG. 2 illustrates a perspective view of the detachable coupling of a mount connector of an example rack mount and a device connector.

FIG. 2 illustrates a perspective view 200 of a detachable coupling between a mount connector 230 and a device connector 220. Mount connector 230 can be configured to facilitate power and/or data transmission between the patient monitor (not shown) detachably secured to the monitor mount 110 and the physiological patient parameter measurement device 210 detachably secured to the physiological patient parameter measurement device mount 130.

A physiological patient parameter measurement device 210 can include a device connector 220. As illustrated in FIG. 2, device connector 220 can be partitioned into quadrants 222, 224, 226, 228. Each quadrant 222, 224, 226, 228 can have a plurality of electrical contacts which are internally wired within physiological patient parameter measurement device 210 to transmit either power and/or data in accordance with a predetermined pin-out of physiological patient parameter measurement device 210. Electrical contacts can include a pin, receptacle, socket, pad, or any other electrical means used in a connector for electrically connecting one connector to a mating connector. More specifically, each quadrant 222, 224, 226, 228 has a plurality of electrical receptacles which are a type of electrical contact. The predetermined pin-out can define a number of electrical contacts within each quadrant of a connector, physical location of each electrical contact within each quadrant, as well as a function of each electrical pin. In the example illustrated in FIG. 2, device connector 220 is a female connector having four electrical sockets in each quadrant. Each electrical socket can be configured to accept a male (mating) connector such as mount connector 230. Quadrants 222, 224 can each have redundant pin-outs such as a pin-out A. Quadrants 226, 228 can each have redundant pin-outs such as a pin-out B. Pin-out A can be electrically different than pin-out B. Mount connector 230 can also be partitioned into quadrants, similar to that of device connector 220. However, only a portion of the partitions can include one or more male electrical contacts to facilitate electrical connections between mount connector 230 and device connector 220. More specifically, device connector 220 includes a plurality of electrical pins as electrical contacts. In the example illustrated in FIG. 2, mount connector 230 is a male connector having quadrants 232, 234, 236, 238. Quadrant 234 can be electrically configured to have pin-out A and quadrant 238 can be electrically configured to have pin-out B. Quadrants 234, 238 are nonadjacent to each other. Quadrants 232 and 236 can have no electrical pins. Quadrants 232, 236 are nonadjacent to each other.

In one variation, such as the one illustrated in FIG. 2, physiological patient parameter measurement device 210 can be oriented in a vertical direction or a horizontal direction. Device connector 220 and mount connector 230 can be keyed connectors which include one or more keyed quadrants, such as quadrants 222, 224, 234. With keyed quadrants, specific orientations of physiological patient parameter measurement device 210 can be required in order to align pin-out A of device connector 220 with pin-out A of mount connector 230 and pin-out B of device connector 220 with pin-out B of mount connector 230. Physiological patient parameter measurement device 210 can be oriented horizontally to position within vertically oriented physiological patient parameter measurement device mount 130a, as illustrated in FIG. 2. In such orientation, quadrant 234 can be detachably secured and electrically coupled to quadrant 224, as facilitated by quadrant 234 being a keyed quadrant. and quadrant 238 can be detachably secured and electrically coupled to quadrant 228. Quadrants 222, 226 can be secured to quadrants 232, 236, respectively. However since quadrants 232, 236 have no electrical pins, there is no electrical coupling.

As physiological patient parameter measurement device 210 contains a second keyed quadrant 222, physiological patient parameter measurement device 210 can be rotated 90 degrees counter-clockwise (e.g., a vertical orientation of physiological patient parameter measurement device 210) to align quadrant 222 to detachably couple to quadrant 234. As previously discussed, mount connector 230 can remain stationary, affixed to articulating leg 120 so as not to modify the orientation of mount connector 230 and its quadrants 232, 234, 236, 238. As a result, when physiological patient parameter measurement device 210 is rotated to be in a vertical orientation to facilitate coupling of quadrant 222 with quadrant 234, a horizontally oriented physiological patient parameter measurement device mount 130b is required. Quadrants 222, 224 can have redundant internal wiring so as to provide the same electrical coupling when either quadrant 222 or 224 is coupled to quadrant 234. The keying of quadrant 234 restricts quadrants 226, 228 from being inadvertently coupled to quadrant 234 due to its geometric misalignment.

A patient monitor that can be detachably coupled to monitor mount 110 and/or physiological patient parameter measurement device 210 can be used to monitor various physiological parameters for a patient. Physiological patient parameter measurement device 210 can be coupled between one or more physiological sensors and a patient. Physiological patient parameter measurement device 210 can include one or more bays for receiving and/or securing patient parameter measurement detachable pods. Such physiological parameters can be transmitted between patient and the patient monitor and/or physiological patient parameter measurement device 210, for example, via a plurality of cables. With such a variation, the patient monitor and/or physiological patient parameter measurement device 210 can include a sensor interface that can connect via wired and/or wireless interfaces to one or more physiological sensors and/or medical devices (e.g., electrocardiogram (ECG) electrodes, $SPO_2$ sensor, blood pressure cuffs, apnea detection sensors, respirators, etc.) associated with the patient. The patient monitor and/or physiological patient parameter measurement device 210 can include one or more processors (e.g., programmable data processors, etc.) which can execute various instructions stored in memory of the patient monitor and/or physiological patient parameter measurement device 210. The patient monitor and/or physiological patient parameter measurement device 210 can additionally include a communications interface which allows the patient monitor and/or physiological patient parameter measurement device 210 directly or indirectly to access one or more computing networks. The communications interface can include various network cards/interfaces to enable wired and wireless communications with such computing networks. The communications interface can also enable direct (i.e., device-to-device, etc.) communications (i.e., messaging, signal exchange, etc.).

The patient monitor and/or physiological patient parameter measurement device 210 can include an electronic visual display. Various data and graphical user interfaces can be conveyed to a user via the electronic visual display. This information can, for example, relate to the measured physiological parameters of a patient transmitted across one or more of a plurality of cables and the like (e.g., blood pressure, heart related information, pulse oximetry, respiration information, etc.). Other types of information can also be conveyed by the electronic visual display. In some variations, the electronic visual display includes a touch screen interface.

Figure 3B:
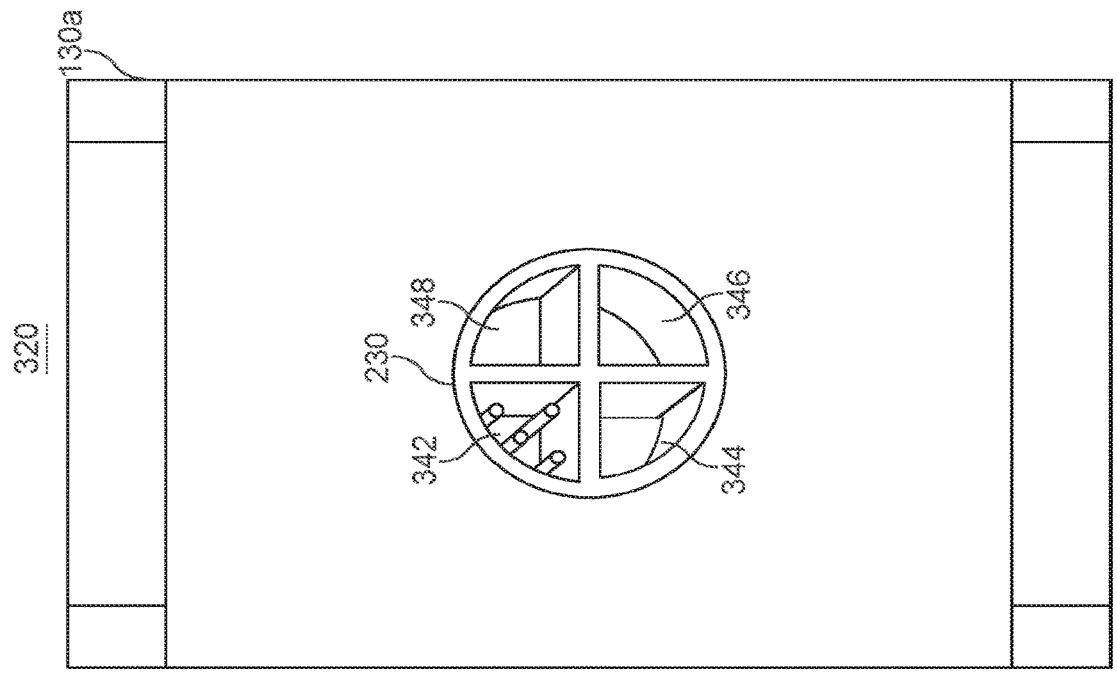
FIG. 3B illustrates a front view of yet another example of a vertically oriented physiological patient parameter measurement device mount and mount connector.
Figure 3A:
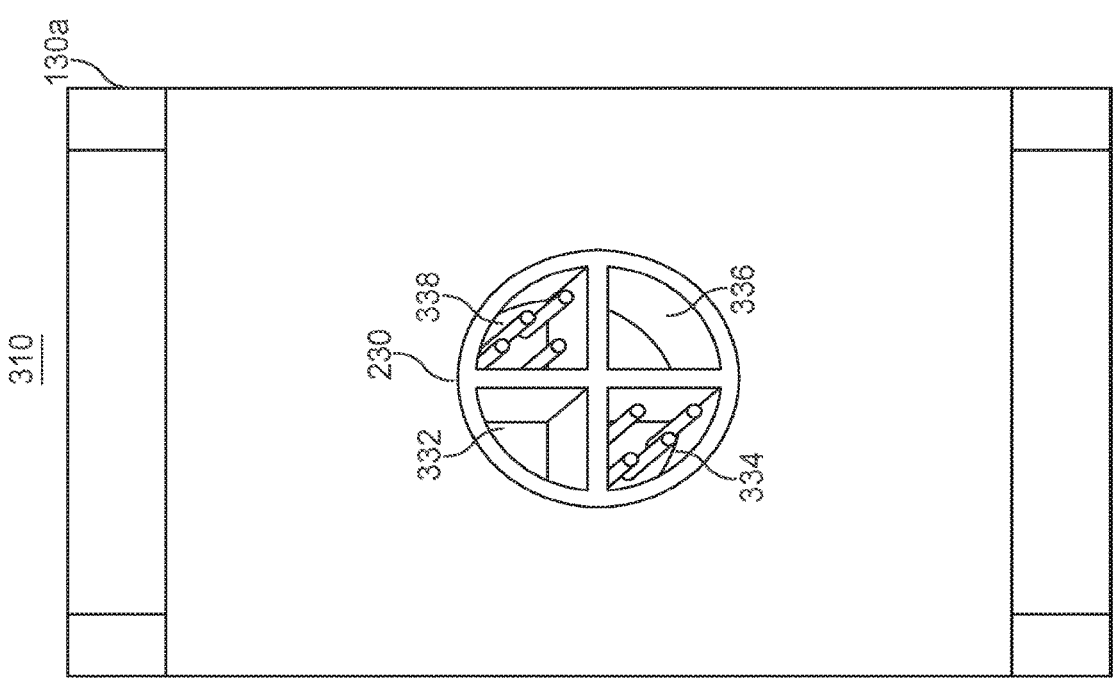
FIG. 3A illustrates a front view of another example of a vertically oriented physiological patient parameter measurement device mount and mount connector.

FIG. 3A illustrates a front view 310 of an example vertically oriented physiological patient parameter measurement device mount 130*a* and mount connector 230. In the variation illustrated in FIG. 3A, mount connector 230 can include quadrants 332, 334, 336, 338. Quadrants 334, 338 can each be electrically configured to have a pin-out C which provides electrical redundancy between quadrants 334 and 338. A mating connector (not shown) can include four quadrants each electrically configured to have pin-out C. Since there is no keying of quadrants 334, 338, a mating connector can be detachably secured to mount connector 230 in any orientation (e.g., 0 degrees, 90 degrees, 180 degrees, 270 degrees). Quadrants 332, 336 having no electrical connection pins, provide no electrical connection to quadrants of mating connector detachably secured thereto.

FIG. 3B illustrates a front view 320 of yet another example vertically oriented physiological patient parameter measurement device mount 130*a* and mount connector 230. In the variation illustrated in FIG. 3B, mount connector 230 can include quadrants 342, 344, 346, 348. Quadrant 342 can be electrically configured to have a pin-out D. A mating connector (not shown) can include four quadrants each electrically configured to have pin-out D. Since there is no keying of quadrant 342, a mating connector can be detachably secured to mount connector 230 in any orientation (e.g., 0 degrees, 90 degrees, 180 degrees, 270 degrees). Quadrants 342, 346, 348 having no electrical connection pins, provide no electrical connection to quadrants of mating connector detachably secured thereto.

It is recognized that while mount connector 230 is illustrated in FIGS. 2 and 3A-3B as a male connector and device connector 220 is illustrated as a female connector, such connectors can be opposite such that mount connector 230 is a female connector configured to receive electrical contacts of device connector 220 which can be a male connector. In other variations, the role of the connectors can be reversed. In other words, mount connector 230 has electrical contacts (e.g., male connection pins) in one or more quadrants and device connector 220 can have electrical receptacles (e.g., a female connector). In yet other variations, mount connector 230 has electrical contacts in all four quadrants while device connector 220 has electrical contacts in only one or two quadrants. As previously described, even though electrical pins and sockets are illustrated in the connectors of FIGS. 2 and 3A-3B, the electrical contacts can include any combination of pins, receptacles, sockets, pads, or any other electrical means used in a connector for electrically connecting one connector to a mating connector.

Figure 4:
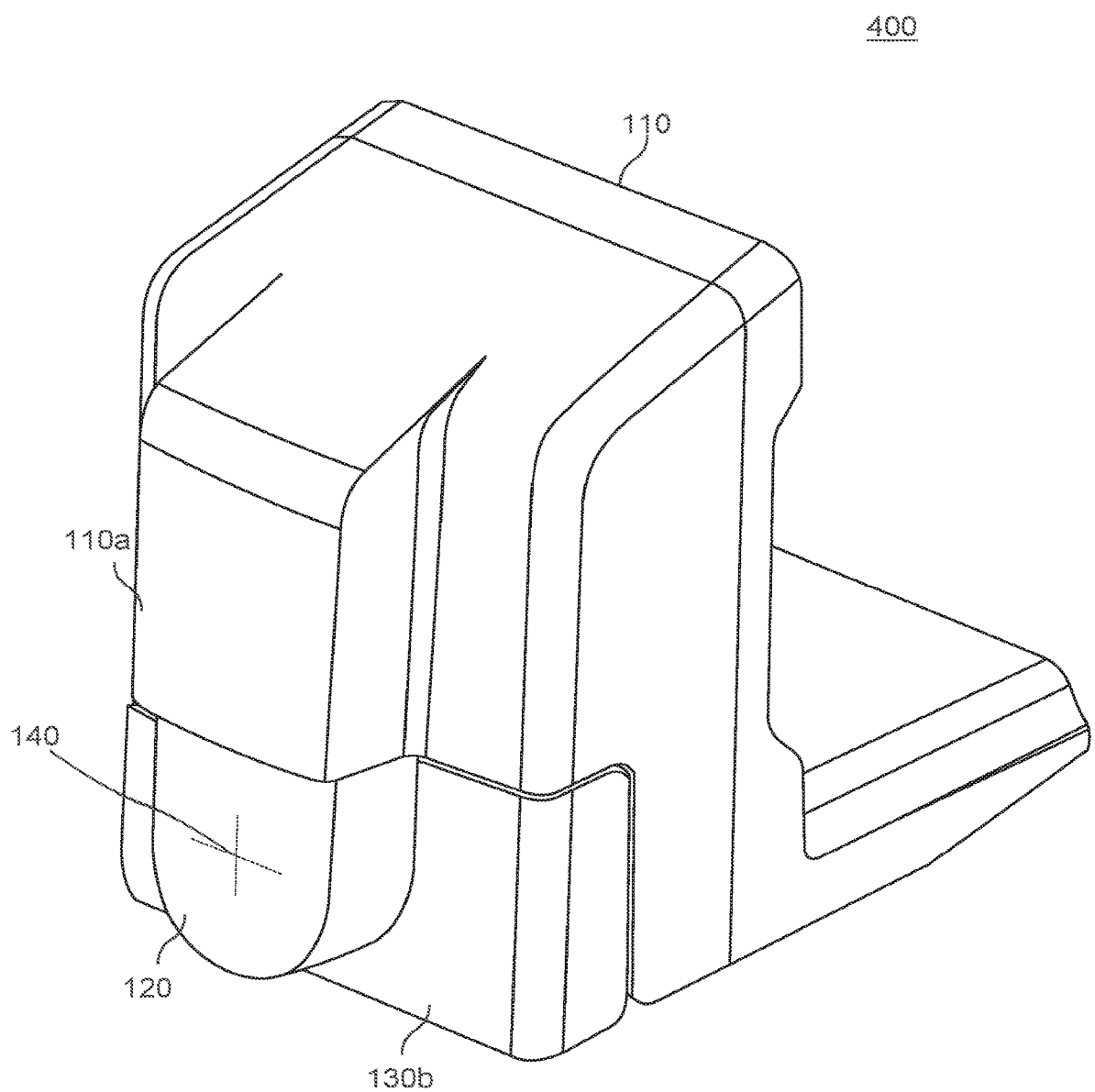
FIG. 4 is a back perspective view of an example rack mount with articulating leg is a stowed position.

FIG. 4 is a back perspective view of rack mount 100 with articulating leg 120 is a stowed position 400. In the stowed position 400, the articulating leg 120 can be fully retracted within the monitor mount 110 and the mount connector 230 is at a distance closest to the monitor mount 110. In some variations, articulating leg 120 can be biased in the stowed position 400. In stowed position 400, the mount connector 230 is blocked and no physiological patient parameter measurement device 210 can be mounted to rack mount 100.

Figure 5:
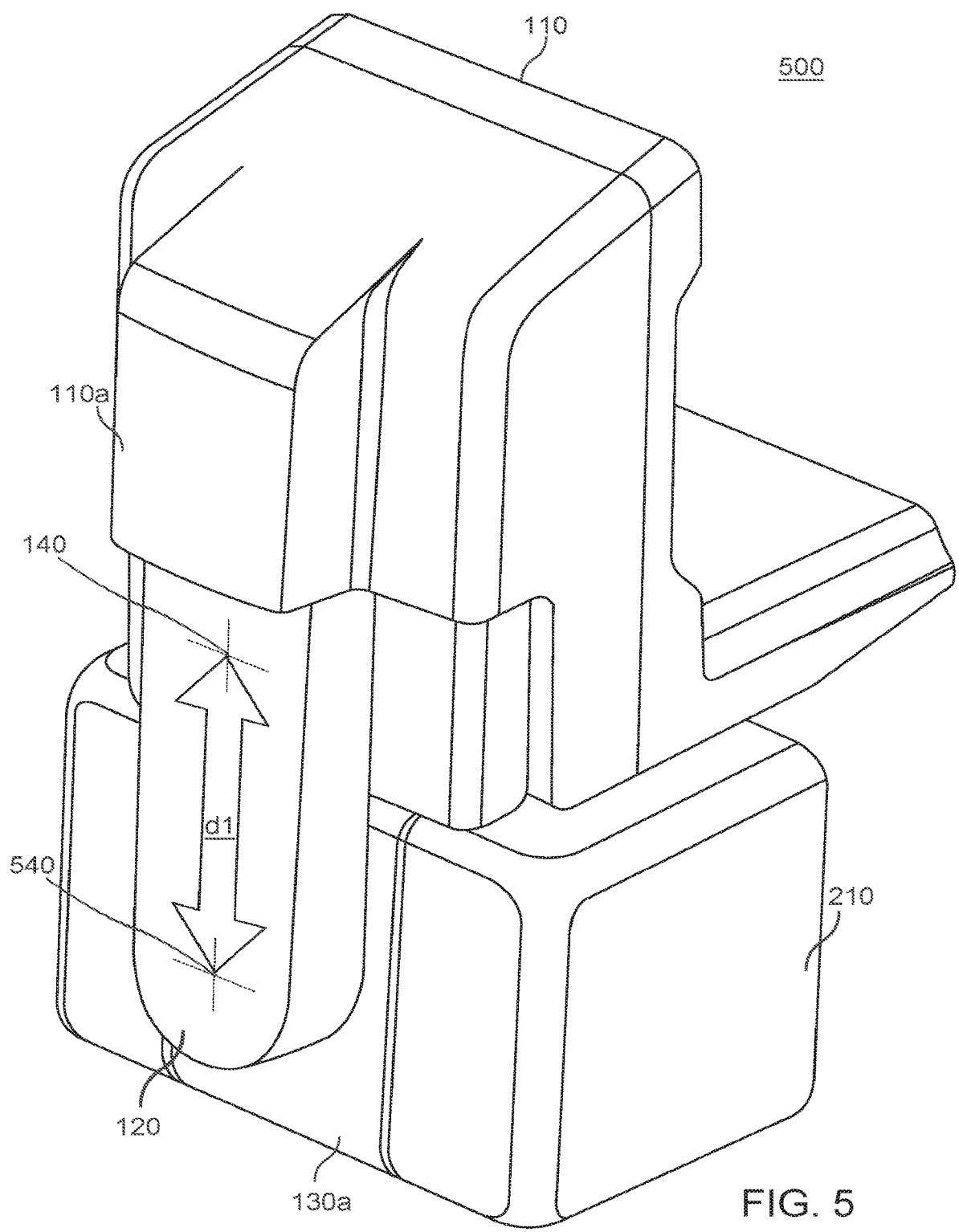
FIG. 5 is a back perspective view of an example rack mount with an articulating leg in an intermediary position between the stowed position of FIG. 4 and fully extended position of FIG. 6.
Figure 6:
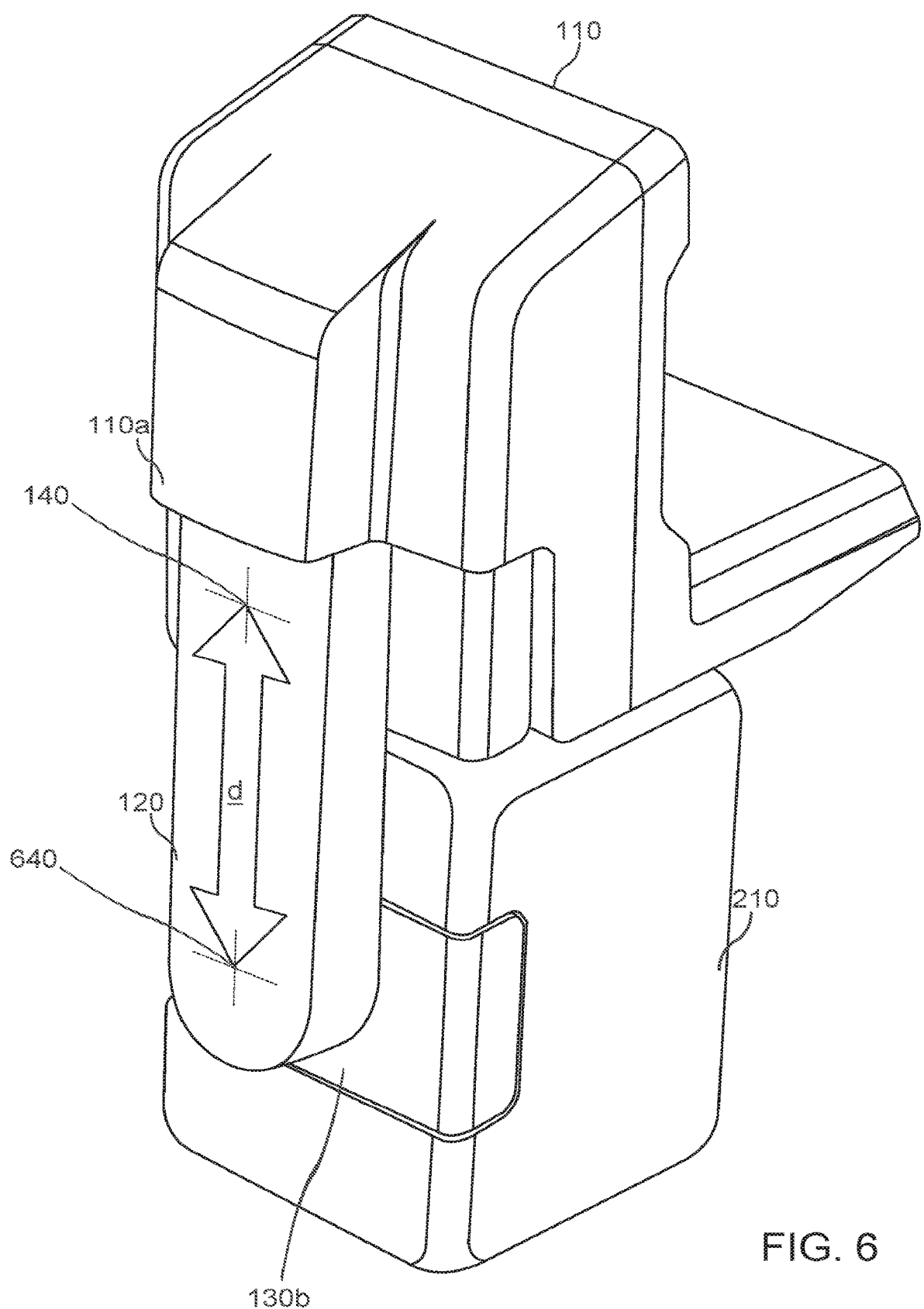
FIG. 6 is a back perspective view of an example rack mount with articulating leg in a fully extended position.

FIG. 5 is a back perspective view of rack mount 100 with articulating leg 120 in an intermediary position 500 between the stowed position 400 and fully extended position 600 of FIG. 6. As illustrated in FIG. 5, in intermediary position 500 vertically oriented physiological patient parameter measurement device mount 130*a*, such as a pod rack, can be detachably coupled to physiological patient parameter measurement device 210, such as a pod module, so as to orient physiological patient parameter measurement device 210 horizontally. In intermediary position 500, articulating leg 120 has a length, d1, measured from center point 140 to stopping point 540.

FIG. 6 is a back perspective view of rack mount 100 with articulating leg 120 in a fully extended position 600. In fully extended position 600, the center point 640 of mount connector can be distance, d, farthest from the monitor mount 110. As illustrated in FIG. 6, in fully extended position 600 horizontally oriented physiological patient parameter measurement device mount 130*b* can be detachably coupled to physiological patient parameter measurement device 210 so as to orient physiological patient parameter measurement device 210 vertically.

While the subject matter described herein relates to connectors that are partitioned into quadrants, it is recognized that the connectors described herein can be partitioned into one or more sections such as halves, thirds, quadrants, or any other delineation.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an un-recited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and sub-combinations of the disclosed features and/or combinations and sub-combinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed:

1. A system of mated connectors, comprising:
   a connector having one or more partitions delineating a plurality of connector sections each having electrical contacts;
   a mating connector detachably secured to the connector, the mating connector having one or more partitions delineating a plurality of mating connector sections having electrical contacts, the mating connector configured to provide electrical coupling to the connector detachably secured thereto;
   wherein the electrical contacts of a first connector section of the plurality of connector sections have a first predetermined pin-out, and the electrical contacts of a second connector section of the plurality of connector sections have a second predetermined pin-out; and
   wherein the electrical contacts of each section of a first pair of the mating connector sections have the first predetermined pin-out and the electrical contacts of each section of a second pair of the mating connector sections have the second predetermined pin-out.

2. The connector of claim 1, wherein the connector is a male connector having one or more electrical connection pins and the mating connector is a female connector having one or more electrical sockets configured to accept the one or more electrical pins of the connector.

3. The connector of claim 1, wherein the mating connector is a male connector having one or more electrical connection pins and the connector is a female connector having one or more electrical sockets configured to accept the one or more electrical pins of the mating connector.

4. The connector of claim 1, wherein the electrical contacts include at least one of pins, receptacles, sockets or pads.

5. The connector of claim 1, wherein the first partition of the connector sections and the second partition of the connector sections are nonadjacent.

6. The connector of claim 1, wherein at least one connector section has no electrical contacts.

7. A connector comprising:
   one or more connector partitions delineating a plurality of connector sections configured to provide electrical coupling to a mating connector having one or more partitions delineating a plurality of mating connector sections, at least one of the plurality of connector sections including a plurality of electrical contacts, and at least one of the plurality of mating connector sections including a plurality of electrical contacts;
   wherein the plurality of electrical contacts of a first section of the plurality of connector sections have a first predetermined pin-out and the electrical contacts of a second section of the plurality of connector sections have a second predetermined pin-out of; and
   wherein the electrical contacts of each section of a first pair of the mating connector sections have the first predetermined pin-out and the electrical contacts of each section of a second pair of the mating connector sections have the second predetermined pin-out.

8. The connector of claim 7, wherein the mating connector includes electrically redundant sections.

9. The rack mount of claim 7, wherein the mating connector includes two electrically different sections.

10. The connector of claim 7, wherein the first partition of the connector sections and the second partition of the connector sections are nonadjacent.

11. The connector of claim 10, wherein at least one remaining connector section has no electrical contacts.

12. A rack mount for providing electrical connections between a patient monitor and one or more physiological sensors affixed to a patient, the rack mount comprising:
    a monitor mount configured to receive and detachably secure to the patient monitor;
    a physiological patient parameter measurement device mount configured to
    (i) rotate and orient in a first orientation or a second orientation; and
    (ii) receive and detachably secure a physiological patient parameter measurement device; and
    a mount connector affixed to the monitor mount, the mount connector comprising one or more sections configured to provide electrical coupling between the patient monitor and the physiological patient parameter measurement device detachably secured to the mount connector.

13. The rack mount of claim 12, wherein the monitor mount includes an articulating leg enclosed within at least a portion of the monitor mount at a first end of the monitor mount and configured to retract and extend between at least two positions, the monitor mount affixed to a second end of the articulating leg.

14. The rack mount of claim 13, wherein the at least two positions includes an extended position with the articulating leg fully extended in a vertical direction and the mount connector is at a distance farthest from the monitor mount.

15. The rack mount of claim 12, wherein the physiological patient parameter measurement device includes a device connector configure to receive the one or more sections of the mount connector.

16. The rack mount of claim 12,
    further comprising:
        the patient monitor; and
        the physiological patient parameter measurement device; and
    wherein:
        the patient monitor is detachably secured to the monitor mount; and
        the physiological patient parameter measurement device is coupled between the one or more physiological sensors and the physiological patient parameter measurement device.

17. The rack mount of claim 12,
    further comprising:
        the patient monitor detachably secured to the monitor mount; and
        the physiological patient parameter measurement device detachably secured to the physiological patient parameter measurement device mount; and
    wherein:

the mount connector is configured to facilitate power, data transmission, or both power and data transmission between the patient monitor and the physiological patient parameter measurement device.

18. The rack mount of claim 12, wherein the mount connector is a mail connector having one or more electrical connection pins and the device connector is a female connector having one or more electrical receptacles configured to accept the one or more electrical pins of the mount connector.

19. The rack mount of claim 12, wherein the mount connector includes electrically redundant sections.

20. The rack mount of claim 12, wherein the mount connector includes two electrically different sections.

* * * * *